United States Patent [19]

Nagata et al.

[11] Patent Number: 4,871,440

[45] Date of Patent: Oct. 3, 1989

[54] BIOSENSOR

[75] Inventors: Yasuhiro Nagata, Kusatsu; Hidetaka Fujimura, Kyoto, both of Japan

[73] Assignee: Daiken Industries, Ltd., Osaka, Japan

[21] Appl. No.: 215,756

[22] Filed: Jul. 6, 1988

[30] Foreign Application Priority Data

Jul. 6, 1987 [JP] Japan .................................. 62-168181

[51] Int. Cl.$^4$ ........................ G01N 27/54; C12Q 1/00; C12Q 1/54
[52] U.S. Cl. ................................... 204/403; 204/412; 204/415; 435/288; 435/817
[58] Field of Search ............... 204/272, 403, 412, 415; 435/288, 817

[56] References Cited

U.S. PATENT DOCUMENTS

| 4,092,233 | 5/1978 | Clemens et al. | 204/403 |
| 4,324,257 | 4/1982 | Albarda et al. | 128/635 |
| 4,356,074 | 10/1982 | Johnson | 204/403 |

Primary Examiner—John F. Niebling
Assistant Examiner—David G. Ryser
Attorney, Agent, or Firm—Wenderoth, Lind & Ponack

[57] ABSTRACT

The present invention provides a biosensor which is arranged to generate an electric signal corresponding to an object to be measured. The biosensor is provided with a foundation electrode which is comprised of a working electrode, a reference electrode and a counter electrode, and on the surface of which is placed an enzyme film fixed with physiologically active material, so that an electric signal corresponding to the object to be measured is generated in the foundation electrode on the basis of the result of the enzyme reaction.

15 Claims, 4 Drawing Sheets

BIOSENSOR

BACKGROUND OF THE INVENTION

The present invention generally relates to a biosensor and more particularly, to a biosensor which is provided, on a foundation electrode, with an active film having physiologically active material fixed thereonto, so as to generate an electric signal corresponding to an object material to be measured on the basis of the result of the activation reaction in the foundation electrode.

Since such characteristics of the physiologically active material have been noticed that it can detect considerably complicated organic compounds, protein or the like with high sensitivity and selectively, studies have been conducted with the use of the physiologically active material, in other words, by forming a biosensor which has the physiologically active material fixed onto the surface of a foundation electrode, thereby to measure the organic compounds, protein, etc.

When the objective material to be measured is measured by the use of the above-described biosensor, the oxidation and reduction or the like of the objective material have been generally carried out in the presence of the physiologically active material, so that the amount of the formed material or the lost material has been measured, thereby to measure the density of the objective material. The aforementioned foundation electrode is roughly classified into two types, namely, the two-electrode type as shown in FIG. 11 and three-electrode type as shown in FIGS. 12 and 13.

More specifically, the two-electrode type of FIG. 11 has a working electrode 31 made of platinum group metal or the like and a counter electrode 32 made of silver or the like which is spaced a predetermined distance from the working electrode 31. It is so arranged according to this type of the foundation electrode that a current signal is generated corresponding to the amount of the material formed or lost as the result of the reaction between the two electrodes.

Accordingly, the density of the objective material can be measured on the basis of the thus-obtained current signal.

In the above-described type of the foundation electrode, however, it is difficult to stabilize the potential between both the electrodes. And, it is general that the potential between the two electrodes is tried to be stabilized by making the area of the counter electrode 32 sufficiently large with respect to the working electrode 31, resulting in bulky structure of the foundation electrode as a whole. Moreover, the counter electrode is generally made of a precious metal, and therefore the foundation electrode itself becomes expensive in accordance with the increase of the size or the area of the precious counter electrode.

On the other hand, according to the threeelectrode type shown in FIGS. 12 and 13, the counter electrode 32 and a reference electrode 33 are placed in symmetry with respect to the working electrode 31, and a bias voltage corresponding to the change of the potential of the counter electrode 32 is applied between the counter electrode 32 and the reference electrode 33 by a direct current source 34 and an operational amplifier 35.

Accordingly, even when the counter electrode 32 has not so large an area, the potential stability can be enhanced, and consequently, the density of the object material is able to be measured with remarkable accuracy on the basis of the obtained current signal.

However, the density of the objective material can not be measured correctly under every condition. For example, so long as the density of the objective material is measured using the balanced current, that is, the measurement is stationary and regular, the density of the objective material is correctly measured. On the contrary, when the measurement of the density of the objective material is carried out on the basis of the change rate of the current, the potential follow-up property of the reference electrode 33 gives great influences upon the measurement accuracy. Accordingly, it becomes necessary that the reference electrode 33 and the counter electrode 32 satisfy the same relationship as the working electrode 31 and the counter electrode 32 of the earlier described two-electrode type, requiring a bias supply circuit for the reference electrode 33. As a result, the structure of the foundation electrode is unfavorably complicated. This will be described in more detail. When the density of the objective material is measured by the above-described biosensor, in general, it is measured by measuring the amount of material produced or lost as a result of the reaction such as oxidation, reduction, etc. of the objective material in the presence of the physiologically active material. Therefore, the measurable upper limit of the density is dependent on the amount of the material causing the oxidation, reduction, etc., for example, oxygen present in the objective material. Thus, even when the density of the object is measured on the basis of the balanced current, the density of the object, if it is highly dense, can never be detected accurately. For solving such disadvantage as above, it may be considered that the density is measured on the basis of the current primary differential peak value. In this case, however, the follow-up property of the reference electrode 33 is required to be increased so as to obtain accurate current primary differential value. Otherwise, correct density of the objective material can not be measured.

SUMMARY OF THE INVENTION

Accordingly, an essential object of the present invention is to provide a biosensor which is arranged to measure the density of an objective material with high accuracy on the basis of an electric signal generated under the unbalanced condition, with eliminating the above-described disadvantages inherent in the prior art.

In accomplishing the above-described object, according to the present invention, the biosensor has a foundation electrode comprised of a working electrode, a reference electrode and a counter electrode arranged in such a manner that the reference electrode surrounding the larger part of the outer periphery of the working electrode and the counter electrode respectively surround the working electrode, with a bias potential supplied corresponding to the change of the potential of the counter electrode.

It is preferable that the above-described reference electrode and counter electrode surround the working electrode in this order.

It is also preferable that the counter electrode and the reference electrode surround the working electrode in this order, and at the same time, the counter electrode is made of platinum group metal.

Moreover, it is preferable that the above reference electrode is placed concentrically with the working electrode as the center.

It is to be noted that the above-described foundation electrode may be so arranged as to generate an electric signal corresponding to the amount of the material formed by the enzyme reaction, or corresponding to the amount of the material lost by the enzyme reaction.

In the biosensor having the construction as described above, the object to be measured is led to the fixed active film where a predetermined reaction is carried out to produce or lose a particular material. As a result, an electric signal is produced in the foundation electrode and guided outwards.

Since the foundation electrode is constructed by the working electrode, the counter electrode and the reference electrode which surrounds the larger part of the working electrode, the potential follow-up property of the reference electrode with respect to the counter electrode in the case of the working electrode as a standard to be enhanced, and moreover, the potential between the working electrode and the reference electrode can be kept maintained at a predetermined value.

More specifically, if the material produced or lost by the enzyme reaction is strikingly fluid, the potential follow-up property of the reference electrode with respect to the change of the potential of the counter electrode is able to be enhanced irrespective of the shape of the reference electrode. However, as the fluidity on the surface of the foundation electrode is fairly poor in general, the potential follow-up property of the reference electrode is bad in the case where the reference electrode is locally disposed in the foundation electrode, thereby to deteriorate in the measuring accuracy of the density of the objective material. However, according to the biosensor of the present invention, the reference electrode is so designed as to surround the greater part of the working electrode, and therefore, even when good fluidity is not observed in the surface of the foundation electrode, namely, partial dispersion is found in the fluidity, the potential follow-up property of the reference electrode with respect to the change of the potential of the counter electrode can be rendered good. Accordingly, the potential between the reference electrode and the working electrode can be kept constant, and the density of the objective material can be measured with high accuracy.

In the case where the reference electrode and the counter electrode surround the working electrode in this order, the current produced between the working electrode and the counter electrode promptly influences the reference electrode, thereby to remarkably improve the potential follow-up property of the reference electrode.

On the contrary, in the case where the counter electrode and the reference electrode surround the working electrode in this order, and at the same time the counter electrode is made of platinum group metal, the counter electrode displays good electrode characteristic, with stabilizing output characteristics so that the density of the objective material can be measured with high accuracy.

Further, if the above-described reference electrode is provided concentrically with the working electrode centering the working electrode, the current produced between the working electrode and the counter electrode exercises positive influences onto the reference electrode, thereby greatly improving the potential follow-up property of the reference electrode.

Moreover, whether the above foundation electrode generates an electric signal corresponding to the amount of the material produced by the enzyme reaction or the foundation electrode is arranged to generate an electric signal corresponding to the amount of the material lost as a result of the enzyme reaction, the similar effects as above can be achieved.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE INVENTION

Figure 1:
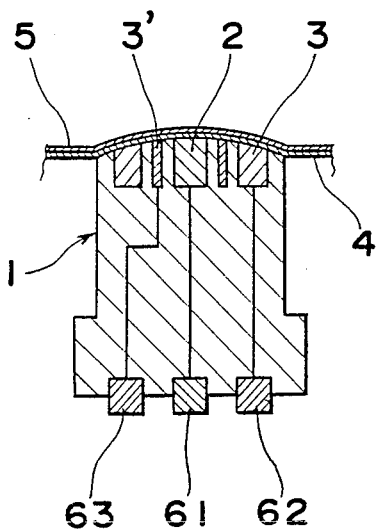
FIG. 1 is a cross-sectional view of a biosensor according to one preferred embodiment of the present invention.

Before the description of the present invention proceeds, it is to be noted that like parts are designated by like reference numerals throughout the accompanying drawings.

Figure 2:
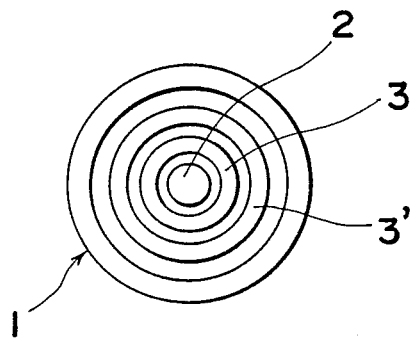
FIG. 2 is a schematic plane view of the biosensor of FIG. 1.
Figure 3:
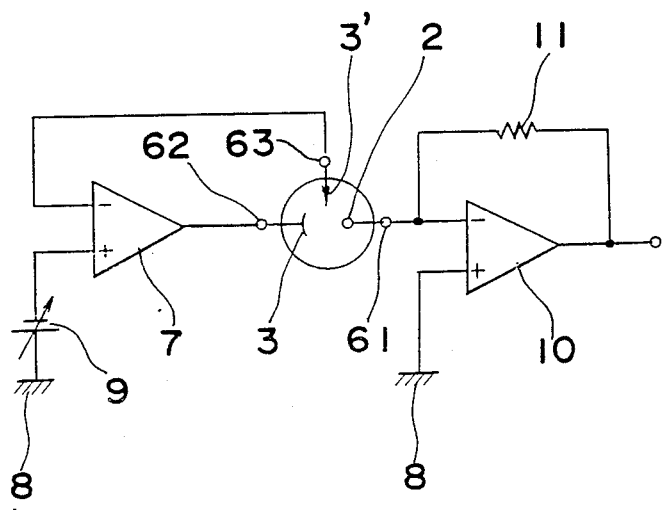
FIG. 3 is a circuit diagram of the biosensor of FIG. 1.

Referring now to FIGS. 1 to 3, there is shown a biosensor according to a first embodiment of the present invention, which comprises an enzyme electrode body 1 having a foundation electrode and an electric circuit for controlling the foundation electrode. The enzyme electrode body includes the foundation electrode on the surface of which is provided an enzyme film fixed with physiologically active material so that an electric signal is generated in the foundation electrode on the basis of the result of the enzyme reaction to measure the density of an objective material. The foundation electrode is comprised of a working electrode 2, a reference electrode 3' and a counter electrode 3 in such a manner that said reference electrode 3' and said counter electrode 3 respectively surround the working electrode 2, said reference electrode 3' surrounding the larger part of the outer periphery of said working electrode 2, and a bias potential is arranged to be supplied corresponding to the change of the potential of said counter electrode. Said counter electrode 3 and said reference electrode 3' respectively surrounded said working electrode 2 in this order, as shown in FIG. 2, and said counter electrode 3 is made of platinum group metal.

The enzyme electrode body 1 is convexed at one side of the surface and has the working electrode 2 made of Pt, and ring-shaped reference electrode 3' and counter electrode 3 both made of Ag arranged in this order in such a manner as to be exposed outwards at the convexed surface. The enzyme electrode is further provided with an enzyme film 4 which is fixed with glucose oxydase (hereinafter referred to as GOD) and, a dispersion controll film 5 which is made of cellophane or the like, in a manner to cover the abovedescribed convexed surface. Moreover, there are signal take-out terminals 61 to 63 respectively connected to the working electrode 3. Also, the terminals are adapted to be connected with external device of the electric circuit such as amplifiers 7, 10 and resistance 11 as shown in FIG. 3.

Accordingly, in the above-described construction, when the enzyme reaction, such as a step of [glucose $+ O_2 + H_2O \xrightarrow{GOD} gluconic\ acid + H_2O_2$], takes place in the fixed enzyme film 4, a current corresponding to the amount of the generated $H_2O_2$ is produced between the working electrode 2 and the counter electrode 3 which is in turn taken outside from the signal take-out terminals 61 and 63.

FIG. 3 schematically shows the electric current adapted to supply bias to the biosensor of FIG. 1. In the electric circuit, the operational amplifier 7 which has its output terminal connected to the counter electrode 3 through the signal take-out terminal 62 has its (−) input terminal connected to the reference electrode 3' via the signal take-out terminal 63. Moreover, a direct current source 9 for reverse bias is connected between a (+) input terminal of the operational amplifier 7 and the earth 8. Also, the operational amplifier 10 has its (−) input terminal connected to the working electrode 2 through the signal take-out terminal 61, and at the same time its (+) input terminal connected to the earth 8, with the feed-back resistance 11 connected between the output terminal and the (−) input terminal of the operational amplifier 10.

The operation of the biosensor having the above-described construction will be explained with reference to FIGS. 4 and 5, which shows respectively the relationships between the (−) voltage of (−) input terminal and the positions of three electrodes, and between the (+) voltage of (+) input terminal and the period of time.

Although the potential of each of the electrodes 2, 3' and 3 is not a fixed value since each electrode is not in touch with the earth 8 as it is, the output terminal of the operational amplifier 7 which is connected at the (+) input terminal with the direct current source 9 so as to supply −V bias to the earth 8 is connected to the counter electrode 3 and at the same time, the (−) input terminal of the operational amplifier 7 is connected to the reference electrode 3', so that the potential of the reference electrode 3' can be controlled following the potential change of the counter electrode 3. In this case, since the reference electrode 3' surrounds all over the working electrode 2, the reference electrode 3' is quickly influenced by the potential change of the counter electrode 3 which is caused by the current generated between the working electrode 2 and the counter electrode 3, thereby to achieve good potential follow-up property.

Figure 4:
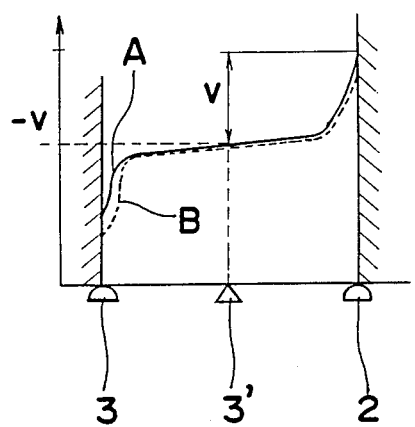
FIG. 4 is a graph showing the changes of voltage to be measured at the positions of electrodes provided in the biosensor of FIG. 1.
Figure 5:
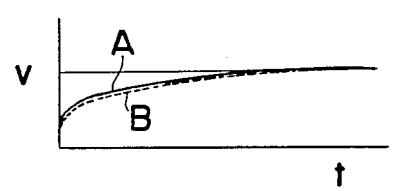
FIG. 5 is a graph showing the changes of voltage to be measured by the biosensor of FIG. 1.

As the working electrode 2 is connected with the (−) input terminal of the operational amplifier 10 which has its (+) input terminal connected to the earth 8, the potential difference between the working electrode 2 and the reference electrode 3' can be kept equal to the electromotive force v of the direct current source 9 with reference to a curve A of the present invention and a curve B of the conventional one in FIGS. 4 and 5.

Explaining in more detail, most of the potential difference generated between the working electrode 2 and the counter electrode 3, as shown in FIGS. 4 and 5, concentrates in the vicinity of the boundary of the working electrode 2 and in the vicinity of the boundary of the counter electrode 3. In the other region, the potential is changed quite gently.

What is important in measuring the density of the objective material is not the potential difference in the vicinity of the boundary of the counter electrode 3, but the potential difference in the vicinity of the boundary of the working electrode 2. Further, since the potential difference in the vicinity of the boundary of the counter electrode 3 may be changed depending on conditions, the potential difference in the vicinity of the boundary of the working electrode 2 should be maintained constant regardless of such change of the potential difference as above in the vicinity of the boundary of the counter electrode 3, and at last it becomes possible to take out a correct signal corresponding to the density of the objective material.

As the potential difference in the vicinity of the boundary of the working electrode 2 varies in accordance with the density of the objective material, a correct signal can be obtained through allowances for the change of the potential difference. The earlier-described electromotive force v is required to be set with considering the above fact.

According to the first embodiment, the potential difference between the reference electrode 3' and the working electrode 2 can be set at v, and moreover, the potential difference between the reference electrode 3' and the working electrode 2 can be kept maintained at v with high follow-up property with respect to the change of the potential difference in the vicinity of the boundary of the counter electrode 3. Therefore, the output voltage from the operational amplifier 10 is a correct value corresponding to the density of the objective material.

Figure 6:
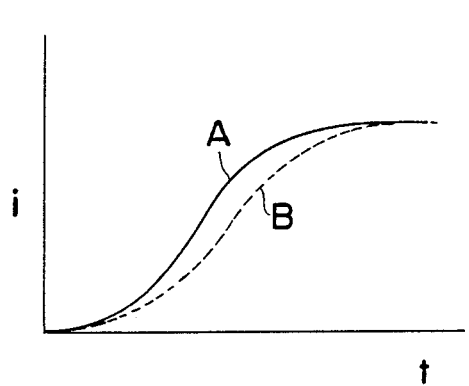
FIG. 6 is a graph showing the changes of current to be measured by the biosensor of FIG. 1
Figure 7:
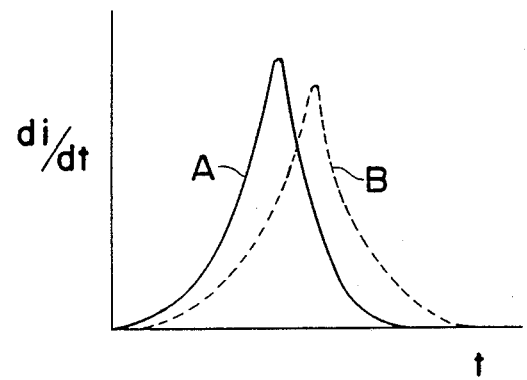
FIG. 7 is a graph showing the current primary differential value of FIG. 6.

FIG. 6 is a graph showing the change of the current value when the density of glucose is measured by the biosensor of the above-described construction in relationship between the electric current and the time from the beginning. FIG. 7 is a graph showing the change of the current primary differential value of the density of FIG. 6. In both FIGS. 6 and 7, the measured data according to the present embodiment is shown by a solid line A, while the data according to the prior art is indicated by a broken line B.

As is clear from the measured data, the follow-up property with respect to the change of the current value is improved in the present embodiment as compared with the prior art, and accordingly, the current primary differential value can be regarded as a value corresponding to the density of the objective material.

Figure 9:
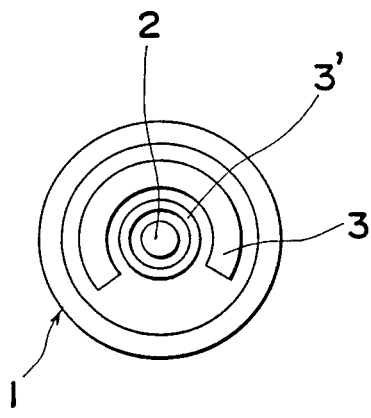
FIG. 9 is a view similar to FIG. 2, but showing a first modification of the biosensor of FIG. 1.
Figure 10:
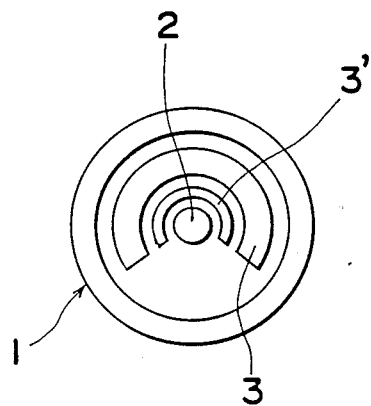
FIG. 10 is a view similar to FIG. 2, but showing a second modification of the biosensor of FIG. 1.

FIG. 9 shows a plan view of a biosensor according to a modification of the first embodiment of the present invention, which is different from the biosensor of the first embodiment simply in the configuration of counter electrode 3. In FIG. 9, the counter electrode 3 is formed in a shape of an arc having a length of more than a half a circle. Also, FIG. 10 is a view similar to FIG. 9, but showing another modification, which is different from the biosensor of the first embodiment simply in the configuration of the counter electrode 3 and reference electrode 3', both formed in the shape of an arc having a length of more than half a circle.

Therefore, the potential difference between the reference electrode 3' and the working electrode 2 can be kept maintained at v also in these modifications, so that considerably correct signal corresponding to the density of the objective material can be obtained.

As is made clear from the foregoing described, a fairly correct signal corresponding to the density of the objective material can be gained both in the first embodiment and the above-mentioned modifications in comparison with the prior art. However, the degree of the correctness of the signal is not the same. As indicated in Table I below, the biosensor of the first embodiment is able to achieve more correct signal. According to the first embodiment, in accordance with the improvement of the potential follow-up property of the reference electrode 3', the dynamic range can be enlarged.

TABLE I (in the case where the glucose density is 150 mg/dl)

|  | First Embodiment of FIG. 1 |
|---|---|
| Output (nA/s) | 64.5 |
|  | 65.4 |
|  | 64.8 |
|  | 63.7 |
|  | 64.2 |
| Average | 64.52 |
| CV (%) | 0.99 |

TABLE II (in the case where the glucose density is 300 mg/dl)

|  | First Embodiment of FIG. 1 |
|---|---|
| Output (nA/s) | 130.3 |
|  | 128.5 |
|  | 129.7 |
|  | 127.7 |
|  | 126.0 |
| Average | 128.44 |
| CV (%) | 1.32 |

In any of the first embodiment and the modifications thereof, the counter electrode 3 is made of Ag, but it may be made of Pt.

When the counter electrode 3 is made of Pt, an output decrease is not observed for a considerably long time after refreshing of the electrode. On the contrary, when the counter electrode 3 is formed of Ag, an output decrease is observed immediately after refreshing of the electrode. Therefore, it is apparent that the electrode characteristic of the Pt electrode as the counter electrode 3 is superior. However, since the Pt electrode is expensive, it is preferable that the counter electrode 3 is formed of Pt in the case of the construction of FIGS. 9 and 10.

Figure 8:
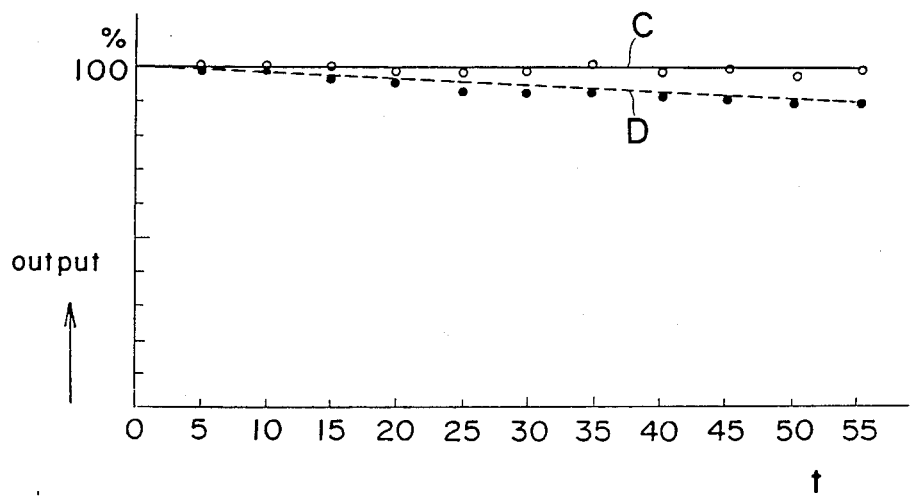
FIG. 8 is a graph showing the changes of output of the biosensor of FIG. 1.
Figure 11:
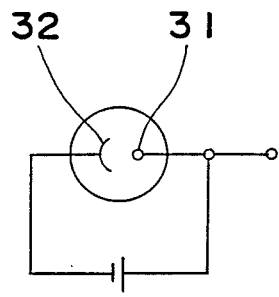
FIG. 11 is a circuit diagram of a conventional biosensor.
Figure 12:
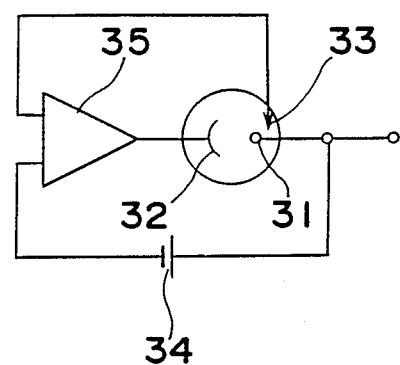
FIG. 12 is a circuit diagram of another conventional biosensor.
Figure 13:
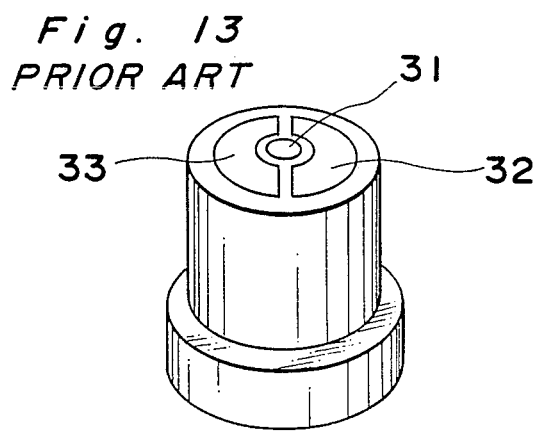
FIG. 13 is a perspective view of the sensor of FIG. 12.

The change of an output after refreshing of the enzyme electrode is shown in the graph of FIG. 8 when the counter electrode 3 is made of Ag, and Pt, respectively. In this case, the construction is that employed in the biosensor of FIG. 2. When the counter electrode 3 is made of Pt, an output is hardly decreased, as shown by a solid line C, whereas, when the counter electrode 3 is made of Ag, about 10% decrease of the output is brought about 55 minutes later from the refreshing of the electrode, as shown by a broken line D. Accordingly, it is clearly seen that the counter electrode 3 is preferable to be made of Pt.

It is to be noted here that the present invention is not restricted to the above-described embodiments. It is possible, for example, that the reference electrode is in such shape that a part of the ring is removed, or in an oval shape, a square shape, etc. Moreover, the center of the lower layer of the reference electrode may not be overlapped with the center of the working electrode, in other words, the reference electrode may not be concentric with the working electrode. Further, the biosensor of the present invention is not only suitable for measuring the density of glucose, but is applicable for measuring, e.g., the density of urea, etc. or the density of the objective material based on the amount of the material produced or lost by the reaction other than $H_2O_2$.

As is described hereinabove, since the biosensor of the present invention is provided with the reference electrode which surrounds the larger part of the working electrode, the potential follow-up property of the reference electrode with respect to the change in the potential of the counter electrode can be improved, resulting in improvement of the measuring accuracy of the density of an object, with enlarged dynamic range being realized.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A biosensor comprising:
    an enzyme electrode body,
    a foundation electrode provided on the enzyme electrode body and including a working electrode, a counter electrode surrounding the working electrode, and a reference electrode surrounding the counter electrode,
    an enzyme film provided on the surface of the foundation electrode and fixed with physiologically active material so that an electric signal is generated in the foundation electrode on the basis of the result of the enzyme reaction to measure the density of an objective material, and an electric circuit including terminals each connected to the respective electrodes and a means for applying a bias potential between the working electrode and the reference electrode corresponding to the change of the potential of the counter electrode.

2. A biosensor as claimed in claim 1, wherein said reference electrode is disposed concentrically with the working electrode as the center.

3. A biosensor as claimed in claim 1, wherein said foundation electrode generates an electric signal corresponding to the amount of material produced by the enzyme reaction.

4. A biosensor as claimed in claim 1, wherein said foundation electrode generates an electric signal corresponding to the amount of material lost by the enzyme reaction.

5. A biosensor having a foundation electrode on the surface of which is provided an enzyme film fixed with physiologically active material so that an electric signal is generated in the foundation electrode on the basis of the result of the enzyme reaction to measure the density of an objective material, wherein said foundation electrode is comprised of a working electrode, a reference electrode and a counter electrode in such a manner that said reference electrode and said counter electrode respectively surround at least part of the working electrode, said reference electrode surrounding the larger part of the outer periphery of said working electrode, and a bias potential is arranged to be supplied corresponding to the change of the potential of said counter electrode.

6. A biosensor as claimed in claim 5, wherein said reference electrode is disposed concentrically with the working electrode as the center.

7. A biosensor as claimed in claim 5, wherein said foundation electrode generates an electric signal corresponding to the amount of material produced by the enzyme reaction.

8. A biosensor as claimed in claim 5, wherein said foundation electrode generates an electric signal corresponding to the amount of material lost by the enzyme reaction.

9. A biosensor as claimed in claim 1 or 5, wherein said reference electrode and said counter electrode respectively surround said working electrode in this order.

10. A biosensor as claimed in claim 9, wherein said reference electrode is disposed concentrically with the working electrode as the center.

11. A biosensor as claimed in claim 9, wherein said foundation electrode generates an electric signal corresponding to the amount of material produced by the enzyme reaction.

12. A biosensor as claimed in claim 9, wherein said foundation electrode generates an electric signal corresponding to the amount of material lost by the enzyme reaction.

13. A biosensor as claimed in claim 1 or 5, wherein said counter electrode and said reference electrode respectively surround said working electrode in this order, and said counter electrode is made of platinum group metal.

14. A biosensor as claimed in claim 13, wherein said foundation electrode generates an electric signal corresponding to the amount of material produced by the enzyme reaction.

15. A biosensor as claimed in claim 13, wherein said foundation electrode generates an electric signal corresponding to the amount of material lost by the enzyme reaction.

* * * * *

UNITED STATES PATENT AND TRADEMARK OFFICE
CERTIFICATE OF CORRECTION

PATENT NO. : 4,871,440

DATED : October 3, 1989

INVENTOR(S) : Yasuhiro NAGATA et al.

It is certified that error appears in the above-identified patent and that said Letters Patent is hereby corrected as shown below:

In the heading, line [73], for "Daiken", read --Daikin--.

Signed and Sealed this

First Day of January, 1991

Attest:

HARRY F. MANBECK, JR.

*Attesting Officer*  *Commissioner of Patents and Trademarks*